(12) United States Patent
Wong et al.

(10) Patent No.: US 7,695,442 B2
(45) Date of Patent: Apr. 13, 2010

(54) INTEGRATED LANCING TEST STRIP WITH RETRACTABLE LANCET

(75) Inventors: Daniel Wong, Sunnyvale, CA (US); Frank Chan, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1251 days.

(21) Appl. No.: 11/103,871

(22) Filed: Apr. 12, 2005

(65) Prior Publication Data

US 2006/0229532 A1   Oct. 12, 2006

(51) Int. Cl.
A61B 5/00 (2006.01)
B65D 81/00 (2006.01)
A61B 17/14 (2006.01)
A61B 17/32 (2006.01)

(52) U.S. Cl. .................. 600/583; 600/573; 606/181; 606/182

(58) Field of Classification Search .................. 600/573, 600/575–584; 606/181–185
See application file for complete search history.

(56) References Cited

U.S. PATENT DOCUMENTS

| | | | |
|---|---|---|---|
| 2,866,542 A | 12/1958 | Svirchev | |
| 2,998,880 A | 9/1961 | Ladd | |
| 3,669,256 A | 6/1972 | Jacob | |
| 3,910,455 A | 10/1975 | Ferraro | |
| 4,123,840 A | 11/1978 | Rumer, Jr. | |
| 4,627,445 A | 12/1986 | Garcia et al. | |
| 4,637,403 A | 1/1987 | Garcia et al. | |
| 4,787,398 A | 11/1988 | Garcia et al. | |
| 4,915,697 A | 4/1990 | DuPont | |
| 5,029,583 A | 7/1991 | Meserol et al. | |
| 5,035,704 A | 7/1991 | Lambert et al. | |
| 5,070,884 A * | 12/1991 | Columbus et al. | ............ 600/573 |
| 5,318,584 A | 6/1994 | Lange et al. | |

(Continued)

FOREIGN PATENT DOCUMENTS

DE   28 03 345 B1   6/1979

(Continued)

OTHER PUBLICATIONS

U.S. Appl. No. 11/105,209, filed Apr. 13, 2005, Wong et al.

(Continued)

*Primary Examiner*—Max Hindenburg
*Assistant Examiner*—Adam J Eiseman
(74) *Attorney, Agent, or Firm*—Woodard, Emhardt, Moriarty, McNett & Henry LLP (57) ABSTRACT

An integrated lancing test strip device includes a lancet configured to form an incision in tissue and a test strip coupled to the lancet for analyzing body fluid. A retention mechanism acts as a detent to hold the lancet in a static position relative to the test strip before forming the incision. The retention mechanism is configured to release the lancet for retracting the lancet relative to the test strip to reduce smearing of body fluid by the lancet during collection of the fluid with the test strip. In one form, the retention mechanism includes breakable tabs that are broken to release the lancet, and the lancet is retracted via translational movement. The retention mechanism in another form includes one or more dimples that release the lancet when the lancet is retracted via rotational motion. In a further form, the entire integrated device is rotated to collect fluid.

21 Claims, 8 Drawing Sheets

U.S. PATENT DOCUMENTS

| | | | |
|---|---|---|---|
| 5,397,334 A * | 3/1995 | Schenk et al. | 606/182 |
| 5,409,133 A | 4/1995 | Gringer | |
| 5,514,152 A | 5/1996 | Smith | |
| 5,599,351 A * | 2/1997 | Haber et al. | 606/167 |
| 5,779,677 A | 7/1998 | Frezza | |
| 5,779,724 A * | 7/1998 | Werner | 606/167 |
| 5,795,632 A | 8/1998 | Buchalter | |
| 5,871,494 A | 2/1999 | Simons et al. | |
| 5,951,492 A | 9/1999 | Douglas et al. | |
| 5,971,941 A | 10/1999 | Simons et al. | |
| 6,010,519 A | 1/2000 | Mawhirt et al. | |
| 6,036,924 A | 3/2000 | Simons et al. | |
| 6,051,293 A | 4/2000 | Weilandt | |
| 6,120,676 A | 9/2000 | Heller et al. | |
| 6,315,738 B1 | 11/2001 | Nishikawa et al. | |
| 6,332,871 B1 * | 12/2001 | Douglas et al. | 600/583 |
| 6,349,229 B1 | 2/2002 | Watanabe et al. | |
| 6,537,257 B1 | 3/2003 | Wien | |
| 6,561,989 B2 | 5/2003 | Whitson | |
| 6,612,111 B1 | 9/2003 | Hodges et al. | |
| 6,616,616 B2 | 9/2003 | Fritz et al. | |
| 6,620,112 B2 | 9/2003 | Klitmose | |
| 6,783,502 B2 | 8/2004 | Orloff et al. | |
| 7,150,755 B2 * | 12/2006 | Levaughn et al. | 606/181 |
| 7,192,405 B2 * | 3/2007 | DeNuzzio et al. | 600/583 |
| 2002/0103499 A1 | 8/2002 | Perez et al. | |
| 2002/0177761 A1 | 11/2002 | Orloff et al. | |
| 2002/0177763 A1 | 11/2002 | Burns et al. | |
| 2003/0050573 A1 * | 3/2003 | Kuhr et al. | 600/567 |
| 2003/0060730 A1 * | 3/2003 | Perez | 600/576 |
| 2003/0144608 A1 | 7/2003 | Kojima et al. | |
| 2003/0153939 A1 | 8/2003 | Fritz et al. | |
| 2003/0191415 A1 | 10/2003 | Moerman et al. | |
| 2003/0211619 A1 | 11/2003 | Olson et al. | |
| 2003/0212344 A1 | 11/2003 | Yuzhakov et al. | |
| 2004/0034318 A1 | 2/2004 | Fritz et al. | |
| 2004/0064068 A1 | 4/2004 | DeNuzzio et al. | |
| 2004/0102717 A1 | 5/2004 | Qi | |
| 2004/0106941 A1 | 6/2004 | Roe et al. | |
| 2004/0120848 A1 | 6/2004 | Teodorczyk | |
| 2004/0127818 A1 | 7/2004 | Roe | |
| 2004/0127819 A1 | 7/2004 | Roe et al. | |
| 2004/0127929 A1 * | 7/2004 | Roe | 606/181 |
| 2004/0186394 A1 | 9/2004 | Roe et al. | |
| 2004/0215224 A1 * | 10/2004 | Sakata et al. | 606/181 |
| 2004/0225312 A1 * | 11/2004 | Orloff et al. | 606/182 |
| 2005/0033341 A1 * | 2/2005 | Vreeke et al. | 606/181 |
| 2005/0251064 A1 * | 11/2005 | Roe | 600/583 |
| 2005/0277850 A1 | 12/2005 | Mace et al. | |
| 2006/0174592 A1 * | 8/2006 | Chan | 53/442 |

FOREIGN PATENT DOCUMENTS

| | | |
|---|---|---|
| DE | 198 55 465 | 6/1999 |
| EP | 0 199 484 B1 | 10/1986 |
| EP | 1 374 770 A1 | 1/2004 |
| EP | 1402812 A1 | 3/2004 |

OTHER PUBLICATIONS

International Patent Application PCT/EP2006/003272 International Search Report mailed Jul. 7, 2006.

U.S. Appl. No. 11/070,502, filed Mar. 2, 2005, Roe.

International Preliminary Report on Patentability from International Patent Application PCT/EP2006/003272 mailed Apr. 20, 2007.

* cited by examiner

INTEGRATED LANCING TEST STRIP WITH RETRACTABLE LANCET

BACKGROUND

The present invention generally relates to bodily fluid sampling devices and more specifically, but not exclusively, concerns an integrated lancing test strip with a unique retractable lancet.

The acquisition and testing of bodily fluids is useful for many purposes, and continues to grow in importance for use in medical diagnosis and treatment, such as for diabetes, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications, is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

The testing of bodily fluids basically involves the steps of obtaining the fluid sample, transferring the sample to a test device, conducting a test on the fluid sample, and displaying the results. These steps are generally performed by a plurality of separate instruments or devices. Performing these steps can be difficult for patients, especially for patients with limited hand dexterity, such as the elderly, or those suffering the effects of their condition, like diabetes. Diabetics suffer many symptoms that can make self-monitoring difficult. For example, diabetics can sometimes experience numbness or tingling in their extremities, such as their hands, and also, wounds tend to heal more slowly for diabetics. In a typical procedure, the patient first creates an incision in the skin by lancing the skin with a lancet. In order to ensure that a sufficient number of capillaries are cut for supplying an adequate bodily fluid sample, the incision has to usually be deep, which can be rather painful for the patient. Often, the incision still does not provide an adequate amount bodily fluid for the sample, and the patient then must resort to expressing the fluid from the incision. If during expression of the fluid the patient is not careful, smearing of the fluid may occur, which may result in rendering the sample useless. Once a sufficient amount of fluid collects as a droplet on the skin, the patient has to position a test strip over the site such that the test strip contacts and absorbs a sufficient amount of the droplet for testing. Usually the droplet of fluid is quite small, and patients, especially ones with hand motor control problems, may experience great difficulty in positioning the test strip so as to collect a sample from the droplet. As should be appreciated, patients can become frustrated by this procedure, and consequently, they may perform the test less often or may even quit testing altogether.

Recently, integrated lancing test strips have been developed in which a test strip is integrated with a lancet so as to form a single disposable unit. While these integrated units have somewhat simplified the collection and testing of fluid samples, there are still a number of issues that need to be resolved before a commercial unit can be implemented. One issue concerns the interaction between the lancet and the test strip during fluid collection. In one type of design, the lancet is fixed relative to the test strip and extends past the edge of the test strip. During lancing, the entire integrated lancing test strip is fired by a lancing mechanism to form an incision, and after forming the incision, the entire integrated lancing test strip is typically retracted from the skin so that the blade is removed from the incision in order to promote blood flow as well as to dull the pain.

With the lancet fixed relative to the strip, a number of difficulties in sampling the fluid are created. For instance, as noted before, the lancet typically extends from the test strip near the capillary opening for the test strip. At such a position, the blade of the lancet can interfere with the collection of body fluid by smearing the droplet of blood on the skin and/or by drawing blood away from the capillary channel. Further, the distance that the capillary has to be retracted is directly proportional to the length of the lancet blade that extends from the test strip. The greater penetration depth created by longer lancet blades usually increases the amount of blood that is bled from the incision, but the greater length of the lancet necessitates that the test strip be retracted farther away from the skin, which in turn can reduce the chances that the blood will be successfully drawn into the capillary channel of the test strip. Conversely, shorter lancets reduce the distance of the test strip from the skin, but shorter lancets normally produce smaller fluid sample sizes from the incision. Moreover, retraction of the entire integrated device is sometimes inconsistent, thereby leading to some undesirable consequences. If the integrated device is retracted too far from the skin, the capillary channel might not be able to contact the fluid droplet on the skin, thereby resulting an incomplete test or insufficient sample size for testing.

Some previous integrated disposable designs were proposed in which a lancet is fixed to a body that holds a separate sensor, which is then rotated into position to collect body fluid. However, the body for such type of disposable was typically made from an extruded plastic that made them rather bulky and expensive to manufacture. Due to their bulky nature, these types of disposables were difficult to incorporate into magazines, drums, cassettes, cartridges and the like.

To alleviate some of these difficulties, integrated lancing test strips have been developed in which the lancet is moveable relative to the test strip. However, such designs still have a number of drawbacks. One issue concerns maintaining the sterility of the lancet so as to minimize the risk of infection. In practice, conventional plastic or syringe type caps that are used to maintain the sterility of typical lancets cannot be incorporated with the moveable lancet design for several reasons. With typical syringe type caps, the cap encapsulates the lancet, and the cap is removed by pulling or twisting the cap off the lancet. However, by its moveable nature, the removal of the cap from the lancet without destroying the integrated device is difficult or even practically impossible. For instance, as the cap is pulled, the lancet moves, which in turn prevents the removal of the cap, and if pulled too much, the lancet can become dislodged from the rest of the integrated lancing test strip. Another issue with the moveable lancet design concerns the positioning of the capillary opening in the test strip after lancing. During a normal sampling procedure, the end of the test strip contacts the skin during lancing so as to control the penetration depth of the lancet and remains in contact with the skin as the fluid from the incision is collected. However, the pressure exerted by the test strip against the skin can constrict the fluid flow from the incision such that the fluid sample size might be too small for accurate analysis. Other systems retract the test strip from the skin, but this is prone to creating positional errors such that the capillary channel opening can be located too far away from the skin to collect fluid. In either case, safe disposal of the integrated device is always a concern. Since the lancet is moveable, it can sometimes extend from the test strip after lancing, thereby creating a potential cutting hazard. Springs or other biasing mechanisms can be used to bias the lancet inside the device in an unexposed position, but occasionally, the integrated device can be compressed or jarred so that the lancet is exposed to create a puncture hazard after use.

Thus, needs remain for further contributions in this area of technology.

SUMMARY

One aspect of the present invention concerns an integrated lancing test strip device. The integrated lancing test strip device includes a lancet configured to form an incision in tissue and a test strip coupled to the lancet for analyzing body fluid. A retention mechanism acts as a detent to hold the lancet in a static position relative to the test strip before forming the incision. The retention mechanism is configured to release the lancet for retracting the lancet relative to the test strip to reduce smearing of body fluid by the lancet during collection of the fluid with the test strip.

Another aspect concerns a unique method for collecting body fluid. With the method, a lancet is held in a fixed position relative to a test strip in an integrated lancing test strip device. An incision is formed in tissue with at least a portion of the lancet extending from the test strip. The lancet is released from the fixed position, and the lancet is retracted inside the integrated lancing test strip device after the incision is formed. Body fluid from the incision is collected with the test strip after the lancet is retracted.

A further aspect concerns an integrated lancing test strip device that includes means for creating an incision in tissue and means for analyzing body fluid from the incision. The device further includes means for holding the means for creating the incision in relation to the means for analyzing the body fluid and for releasing the means for creating the incision upon application of force.

Still yet another aspect concerns an apparatus that includes an integrated lancing test strip device. The integrated lancing test strip device includes a test strip for analyzing body fluid. The test strip has a capillary channel with an opening for drawing the body fluid via capillary action. The test strip is flat. A lancet is directly coupled to the test strip for forming an incision in tissue. An actuation device is coupled to the integrated lancing test strip device. The actuation device is configured to fire the lancet into the tissue. The actuation device is configured to rotate the lancet away from the incision in order to minimize interference by the lancet as the body fluid from the incision is drawn into the capillary channel of the test strip.

Further forms, objects, features, aspects, benefits, advantages, and embodiments of the present invention will become apparent from a detailed description and drawings provided herewith.

DESCRIPTION OF THE SELECTED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

An integrated lancing test strip or disposable according to one of many embodiments of the present invention includes a test strip and a lancet. The lancet is attached to the test strip so as to be initially in a static (immobilized) position relative to the rest of the test strip, but is able to move inside the device after lancing the skin. In one embodiment, breakable tabs are used to hold the lancet in place, and in another embodiment, protrusions in the device act like detents to engage and hold the lancet in place. This ability to have the lancet fixed in position before lancing, gives the device the ability to use conventional protective caps that maintain the sterility of the lancet. With the lancet fixed in position, the protective cap can be easily pulled or twisted off the lancet, either manually or automatically. Once the cap is removed, the integrated disposable, acting as a lancing member, is fired by a lancing mechanism, thereby creating an incision from which body fluid is sampled. After the incision is created, the lancet is retracted (mobilized) inside the device such that the lancet moves away from the incision, thereby giving a clear path for the capillary channel of the test strip to contact and collect the body fluid. With the clear path, body fluid can then be easily drawn into the capillary channel of the test strip without having the lancet interfere with the sample collection. In one form, the lancet is retracted in a linear fashion, and in another form, the lancet is rotated during retraction. The lancing device, which houses the integrated lancing test strip, includes a firing mechanism for firing the integrated device, a stabilizer bar, a lancet stabilizer arm, and a deflection arm.

The deflection arm enhances sample contact by flexing the integrated disposable in a sweeping motion toward the sample droplet. In still another embodiment, the lancet remains fixed after lancing, but the entire integrated lancing test strip is rotated so that a capillary channel, which is offset from the lancet, is rotated into position over the incision.

Figure 1:
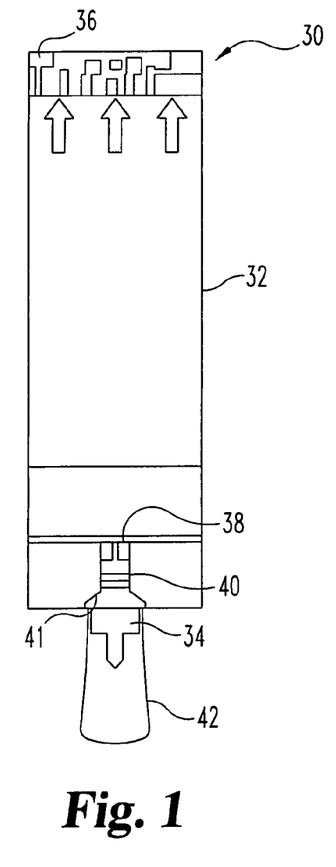
FIG. 1 is a top view of an integrated lancing test strip device according to one embodiment.
Figure 2:
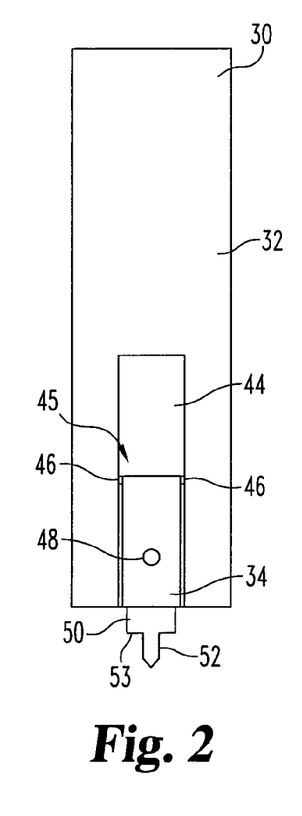
FIG. 2 is a bottom view of the FIG. 1 integrated device with a lancet located in a static position.
Figure 3:
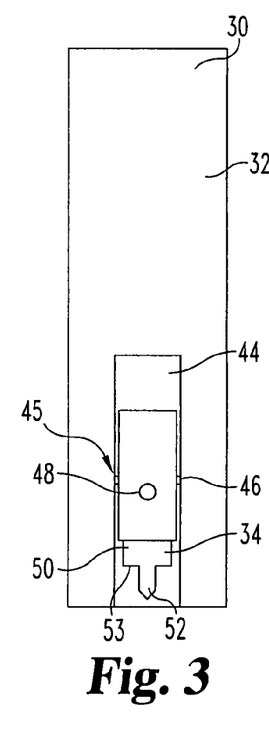
FIG. 3 is a bottom view of the FIG. 1 integrated device with the lancet in a retracted position.

FIGS. 1, 2, and 3 illustrate an integrated lancing test strip device or disposable 30 according to one embodiment of the present invention. As shown in FIG. 1, the integrated device 30 includes a test strip 32 that is coupled to a lancet 34. In the illustrated embodiment, the test strip 32 is an electrochemical type test strip, but it should be recognized that other types of test strips can be used, such as for example colorimetric or optical type test strips, to name a few. The test strip 32 includes a connector portion 36 with electrical contacts that connect the integrated device 30 to a sampling device or meter such that the integrated device 30 is able to transfer the test results to the meter. The test strip 32 further includes an analysis portion or area 38 in which the fluid sample is analyzed. In one form, the analysis portion 38 includes a reagent and electrodes, such as working, counter and reference electrodes, for analyzing the fluid sample. The test strip 32 includes a capillary channel 40 with a capillary channel opening 41 for transporting body fluid to the analysis portion 38. The analysis portion 38 is located in one end of the capillary channel 40, opposite the capillary channel opening 41. The capillary channel 40 is sized and configured to draw body fluid via capillary action from the channel opening 41 onto the analysis portion 38. The capillary channel 40 as shown is Y-shaped, but it is contemplated that the channel 40 can be shaped differently in other embodiments. To assist in drawing fluid, the capillary channel 40 can include a vent opening or slot. Furthermore, the integrated lancing test strip 30 in the illustrated embodiment has a generally flat profile. By being flat, the integrated device 30 can be formed by sandwiching sheets of the various components together to form individual integrated devices 30. The flat shape also allows multiple integrated devices 30 to be combined together into, for example, cassettes, cartridges, magazines, drums and the like so as to allow multiple tests without the need to reload the meter with additional integrated devices 30. As should be recognized, the integrated devices 30 can also be loaded and used in a meter on an individual basis. In one particular form, the test strip 32 includes an ACCU-CHEK® brand test strip (Roche Diagnostics GmbH), but it is envisioned that other types of test strips can be used. Moreover, it is contemplated that the integrated device 30 can have a different overall shape in other embodiments. By way of a non-limiting example, the integrated device 30 in other embodiments can have an overall rounded shape.

With continued reference to FIG. 1, the lancet 34 is encapsulated in a protective cover 42 so as to maintain the sterility of the lancet 34. In one form, the cover 42 is a plastic cap that can be pulled or twisted off the lancet 34 before use. The cover 42 can be manually removed by the user and/or automatically removed by the meter. It is contemplated that the protective cover 42 can come in other forms. For example, the protective cover 42 in another embodiment includes two sheets of film that are peeled from the lancet 34 prior to use. Looking at FIG. 2, the integrated device 30 includes a lancet guide channel 44 in which the lancet 34 is disposed. In one form, a sheet or a layer of material covers the lancet channel 44 so as to keep the lancet 34 inside the lancet channel 44. The lancet channel 44 extends longitudinally along the integrated device 30 so that the lancet is retracted in a linear manner. As will be appreciated, the lancet channel 44 can be shaped differently in other embodiment so that the lancet 34 can be retracted in other manners. The lancet channel 44 in one embodiment is formed directly in the test strip 32, and in another embodiment, the channel 44 is defined by a separate spacer member that is attached to the test strip 32. As should be appreciated, the lancet channel 44 can be defined in other ways. In the illustrated embodiment, the lancet 34 is generally flat, but in other embodiments, the lancet 34 can be rounded or have a different overall shape. In the illustrated embodiment, the lancet channel 44 in which the lancet 34 is received and the opening 41 of the capillary channel 40 are longitudinally aligned with one another on opposite sides of the test strip 32 so that the capillary channel opening 41 is positioned close to the incision formed by the lancet 34 so as to promote fluid collection. As will be appreciated from the description of the other embodiments, the lancet 34 and the capillary channel opening 41 can be offset from one another in other embodiments.

Inside the lancet channel 44, the device 30 has a retention mechanism or structure 45 that acts like a detent mechanism to hold the lancet 34 in place relative to the test strip 32 before lancing, and allows the lancet 34 to be retracted inside the lancet channel 44 after lancing. With the retention structure 45, the protective cover 42 can be easily removed from the lancet 34 without damaging the integrated lancing test strip 30. For instance, if the integrated device 30 did not have the retention mechanism 45, the lancet 34 could be completely removed from the lancet channel 44 by the pulling and/or twisting action as the cover 42 is removed. In the depicted embodiment, the retention mechanism 45 is configured to retain the lancet 34, by friction, within the lancet channel 44 after lancing, as is shown in FIG. 3. This in turn eliminates the need for the cover 42 or some other protective structure from being placed over the lancet 34 after use, and further, reduces the chances of injuries during disposal. Some typical integrated lancing test strip designs with moveable lancets require a spring to retract and bias the lancet within the test strip so that the lancet is covered during disposal. However, springs can be expensive, especially for high volume items like disposable integrated lancing test strips, and further, springs are not always strong enough to retain the lancet within the test strip so as to prevent accidental cuts. As should be recognized, the retention mechanism 45 eliminates the need for springs in the integrated device so that the above-mentioned difficulties are reduced or even eliminated. Although not required, it is contemplated that in other embodiments springs can be used in conjunction with the retention mechanism 45 to retain the lancet 34 within the lancet channel 44.

In the embodiment illustrated in FIGS. 2 and 3, the retention mechanism 45 includes one or more breakable tabs 46 that secure the lancet 34 to the walls of the lancet channel 44. As shown, two breakable tabs 46 connect two opposing sides of the lancet 34 to the test strip 32. The tabs 46 in this embodiment prevent longitudinal movement as well as rotational movement of the lancet 34. After forming an incision, the tabs 46 also serve to retain the lancet 34 inside the integrated device 30 by frictionally engaging the lancet 34. The tabs 46 are constructed to break when a specified force is applied to retract the lancet 34. In one form, the breakable tabs 46 are made of fracturable plastic material that is strong enough to hold the lancet 34 in place during lancing, but is able to break to allow retraction of the lancet 34. It, however, should be appreciated that the tabs 46 can be made of other materials. Moreover, it is envisioned that the retention mechanism 45 can include others types of mechanisms and/or structures for holding the lancet 34 in relation to the test strip 32 so that the lancet 34 can be released by an applied force. For example, the retention mechanism 45 can include an adhesive that is applied between the lancet 34 and the test strip 32. The adhesive holds the lancet 34 in place during lancing, but releases the lancet 34 when a predefined (or greater) force is applied between the lancet 34 and the test strip 32 during retraction. In another embodiment, a ball and spring type detent mechanism is used to hold the lancet 34 in place. It is contemplated that in other embodiments the retention mechanism 45 can be configured to release and make the lancet 34 moveable, once the protective cover 42 is removed from the lancet 34.

The lancet 34 has an engagement hole or opening 48 defined in body 50 of the lancet 34 that is used to engage the lancet 34. Although the engagement hole 48 in the embodiment shown is circular, the engagement hole 48 can be shaped differently in other embodiments and/or include other types of structures for coupling to the lancet 34 to a lancing device. In FIGS. 2 and 3, a lancet tip or blade 52 for puncturing the skin or other tissue extends from the lancet body 50. In the embodiment shown, the lancet body 50 is wider than the lancet tip 52. At the interface between the lancet body 50 and the tip 52, the lancet 34 has a depth penetration edge 53 that limits the penetration of the lancet 34 into the skin or other tissue.

Figure 4:
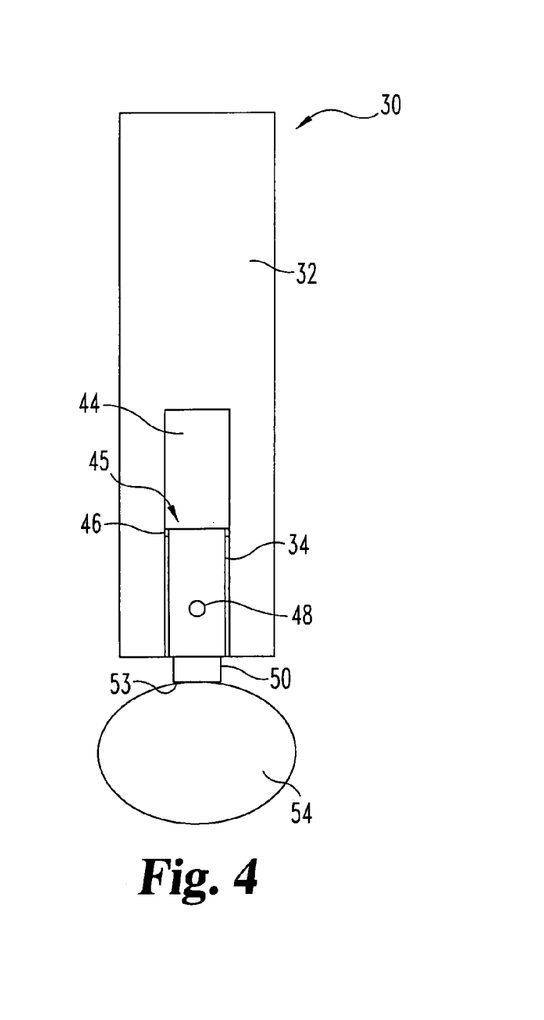
FIG. 4 shows the FIG. 1 integrated device lancing skin to form an incision.

Before lancing, the retention mechanism 45 in one embodiment holds the lancet 34 with the lancet tip 52 extending from the test strip 32, as is illustrated in FIGS. 1 and 2. With this construction, the entire integrated device 30 is fired against the skin, and the tabs 46 are broken as the lancet 34 is retracted inside the lancet channel 44 As depicted in FIG. 4, during lancing, the lock tabs 46 hold the lancet 34 fixed in place such that the lancet tip 50 extends from the test strip 32 as the skin is lanced. The penetration edges 53 on the lancet 34 limit the penetration depth of the lancet tip 52 into skin or tissue 54. The penetration edges 53 also provide a reference surface for vertically spacing the edge of the test strip 32 away from the skin 54, which in turn promotes bleeding from the incision 56. As noted before, contact between the test strip 32 and the skin 54 can create pressure that constricts fluid flow to the incision. By spacing the test strip 32 from the skin 54 in such a manner, the chance of fluid flow constriction is reduced. At the same time, it is ensured that the test strip 32 is not spaced too far away from the skin 54 so as to be unable to collect a sufficient sample of body fluid 58, such as blood, interstitial fluid and other fluids.

Figure 5:
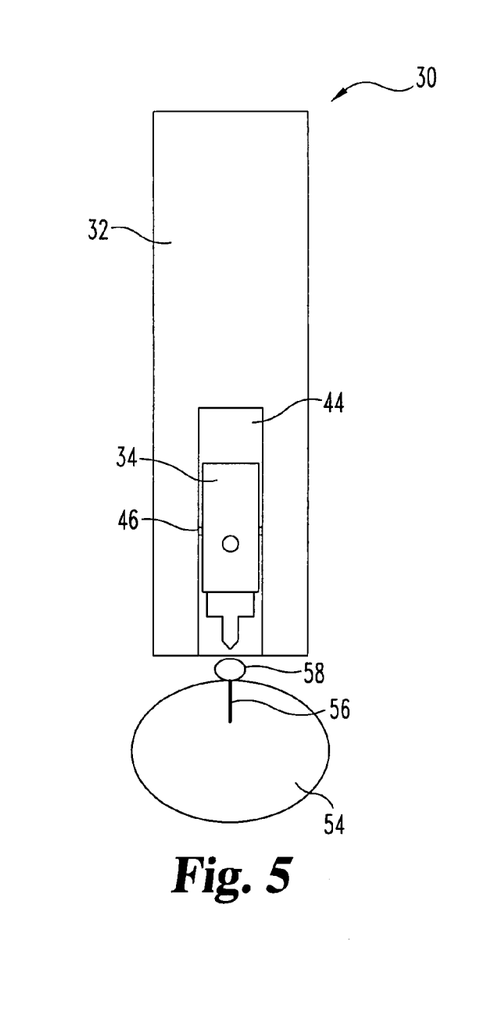
FIG. 5 shows the FIG. 1 integrated device collecting fluid from the incision.

Before lancing the skin 54, the skin 54 can be stimulated to enhance fluid flow, if so desired. After an incision 56 in the skin 54 is formed, the lancet 34 is retracted into the lancet channel 44 of the device 30, as shown in FIG. 5. During retraction, the lancet 34 moves, but the test strip 32 remains vertically stationary relative to the skin 54 so that the spacing between the test strip 32 and the skin 54 is maintained. With the lancet 34 located inside the integrated device 30, the lancet 34 does not interfere with fluid collection. After forming the incision 56, body fluid 58 can be expressed from the incision 56 either manually or automatically in the manners as known to those skilled in the art. As the body fluid 58 bleeds from the incision 56, the fluid 58 is then drawn into the capillary channel 40 via capillary action. As should be recognized, portions of the integrated lancing test strip 30 can be hydrophobic and/or hydrophilic so as to direct fluid flow. The fluid 58 is then drawn to the analysis area 38, where the fluid 58 is analyzed, and the results of the analysis are sent to the meter via the connector portion 36. After retraction of the lancet 34, the tabs 46 help to retain the tip 52 of the lancet 34 within the channel 44 such that the integrated device 30 can be disposed of with minimal risk of accidental puncturing of the skin. By having the position of the lancet 34 fixed relative to the test strip 32 during lancing and allowing the lancet 34 afterwards to retract independently of the test strip 32, the spacing of the test strip 32 from the skin 54 can be accurately set and maintained, thereby promoting collection of the body fluid 58 from the incision 56.

In another embodiment, before lancing, the retention mechanism 45 immobilizes the lancet 34 with the lancet tip 52 positioned inside the integrated device 30, in the manner as shown in FIG. 3. By having the lancet tip 52 positioned inside the integrated device 30 before use, the risk of accidental injury from the lancet 34 is reduced. The opening of the lancet channel 44 can be sealed to maintain sterility and/or the integrated device 30 can be packaged in other manners to maintain sterility. In this embodiment, the tabs 46 are broken during lancing so that the lancet 34 moves relative to the test strip 32 during both extension and retraction. After lancing, the frictional engagement between the breakable tabs 46 and the lancet 34 help to retain the lancet 34 within the integrated device 30.

Figure 6:
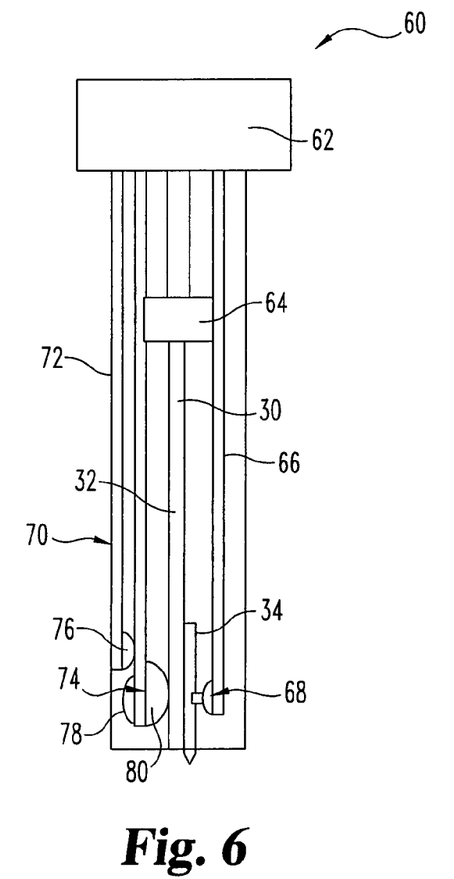
FIG. 6 is a side view of an actuation device for firing the FIG. 1 integrated device.

FIG. 6 illustrates an actuating device (or meter) 60 that is used to fire and retract the integrated lancing test strip device 30 illustrated in FIG. 1. It should be recognized, however, that the device 60 can be used to actuate other types of integrated lancing test strips, such as for the other embodiments described herein. As shown, device 60 includes a lancing mechanism 62 that is used to fire the lancet 34, and a connector 64 that connects the integrated device 30 to the lancing mechanism 62. In one form, the lancing mechanism 62 includes a motor, such as an electric or pneumatic type motor, and in another form, the lancing mechanism 62 is a spring driven type of device. It should be appreciated that the lancing mechanism 62 can include other types of functionally similar devices as would occur to those skilled in the art. The connector 64 engages the strip connector 36 such that the test results can be transferred to a signal converter or meter that is used to process the results. Device 60 further includes a lancet stabilizer/retractor arm 66 with an engagement member or pin 68 that is constructed to engage the engagement hole 48 in the lancet 34. In conjunction with the lancing mechanism 62, the retractor arm 66 is configured to retract the lancet 34 into the integrated device 30. The device 60 further incorporates a deflection mechanism 70 that is used to deflect the test strip 32 so that the capillary channel 40 in the test strip 32 is deflected over the incision 56 to collect body fluid 58.

As depicted, the deflection mechanism 70 includes a deflection arm 72 and a strip stabilizer 74. The deflection arm 72 and the strip stabilizers 74 each include opposing cam surfaces 76, 78 that engage one another to bend the strip stabilizer 74. The strip stabilizer 74 further includes an engagement portion or pillow button (block) 80 that engages the integrated lancing test strip 30. To deflect the test strip 32, the deflection arm 72 is extended by the lancing mechanism 62. As the deflection arm 72 is extended, the cam surface 76 on the deflection arm 72 pushes against the cam surface 78 on the strip stabilizer 74. This action bends the strip stabilizer 74 such that the pillow button 80 pushes against the test strip 32. As a result, the test strip 32 bends so that the opening 41 of the capillary channel 40 wipes across the incision 56.

Figure 7:
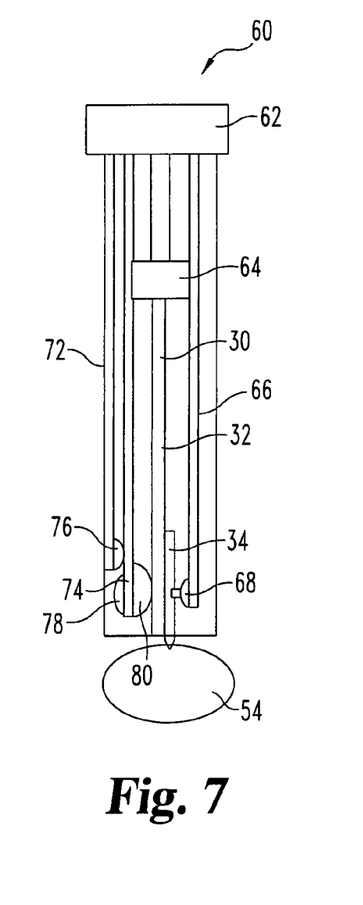
FIG. 7 is a side view of the FIG. 6 device during lancing.
Figure 8:
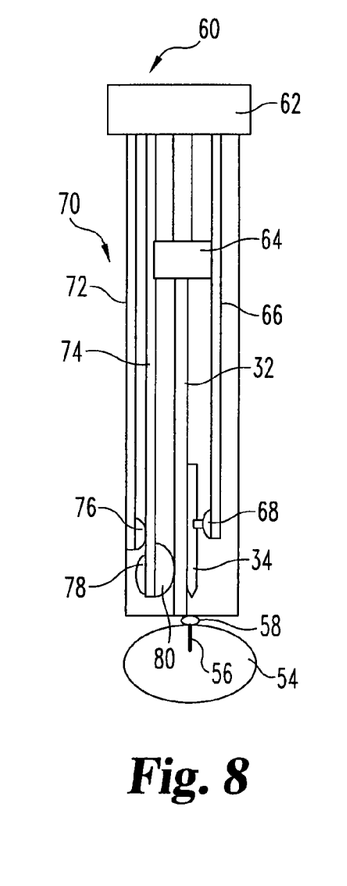
FIG. 8 is a side view of the FIG. 6 device as the lancet is retracted.
Figure 9:
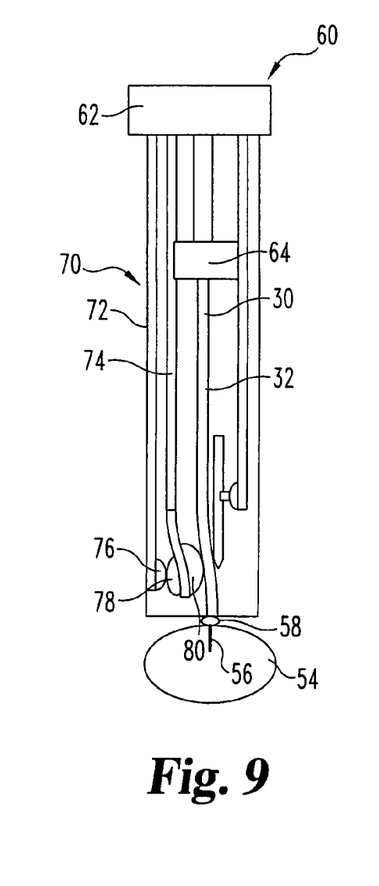
FIG. 9 is a side view of the FIG. 6 device as the FIG. 1 device is wiped across the incision during sampling.

FIGS. 7, 8 and 9 illustrate the operation and configuration of the actuation device 60 during the lancing, retracting and sampling stages, respectively. As illustrated in FIG. 7, the connector 64 along with the retractor arm 66 is fired in unison by the lancing mechanism 62 so that the integrated device 30 is fired against the skin 54. As can be seen in FIG. 8, the lancet 34 forms an incision 56 in the skin 54, and after forming the incision 56, the retractor arm 66 retracts the lancet 34 away from the skin 54, while the connector 64 remains fixed in position. Consequently, the tabs 46 in the lancet channel 44 are broken so that the lancet 34 is able to move relative to the test strip 32, and the lancet 34 is retracted inside the integrated device 30. A droplet of body fluid 58 from the incision 56 forms on the skin 54. To collect the fluid 58, the deflection mechanisms 70 sweeps the test strip 32 over the droplet of fluid 58. It should be noted that by retracting the lancet 34 into the integrated device 30 the overall flexibility of the test strip 32 can increase such that the test strip 32 can be easily bent. Referring to FIG. 9, the lancing mechanism 62 extends the deflection arm 72 towards the skin 54. When the deflection arm 72 extends, the cam surface 76 on the deflection arm 72 pushes against the cam surface 78 on the strip stabilizer 74. This action bends the strip stabilizer 74 such that the pillow button 80 pushes against the test strip 32. Consequently, the test strip 32 bends so that the opening 41 of the capillary channel 40 wipes across the incision 56. The swiping action of the test strip 32 over the incision 56 can occur only once or can be repeated a number of times. The fluid 58 drawn into the capillary channel 40 is analyzed in the manner as described above, and the results from the analysis are sent to the meter through the connector 64.

Figure 10:
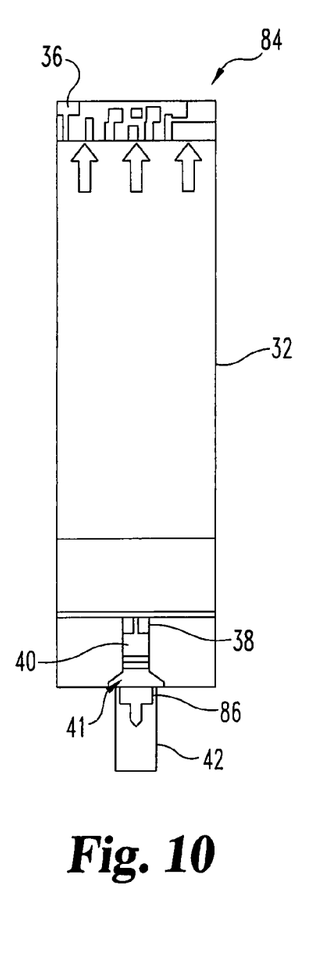
FIG. 10 is a top view of an integrated lancing test strip device according to another embodiment.
Figure 11:
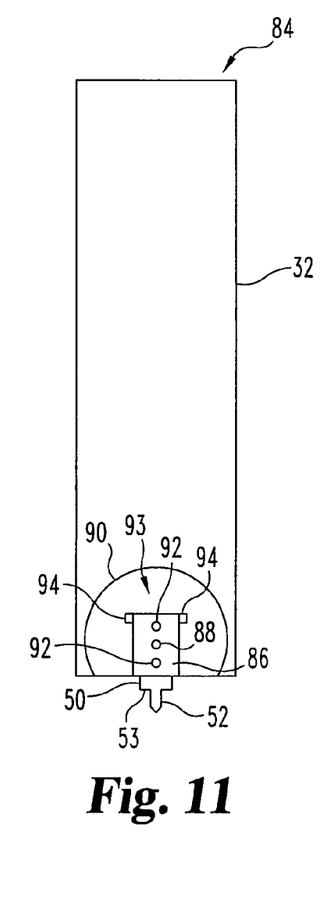
FIG. 11 is a bottom view of the FIG. 10 integrated device.

An integrated lancing test strip device 84 according to another embodiment is illustrated in FIGS. 10 and 11. As can be seen, the integrated device 84 in FIG. 10 shares a number of features in common with the previously described embodiment. For the sake of clarity as well as brevity, these common features will not be described in great detail again, but rather reference is made to the previous discussion of these features. The integrated device 84 includes the test strip 32, like the one described above, with the connector 36 for connecting to a meter. Like before, the test strip 32 has the capillary channel 40 with the capillary opening 41 and the analysis portion 38 for testing the body fluid sample.

On the side opposite the capillary channel 40, the integrated device 84 in FIG. 11 has a lancet 86 that is pivotally coupled to the test strip 32. Instead of retracting the lancet 86 in a longitudinal or linear fashion, the lancet 86 in the illustrated embodiment is retracted in a rotational manner. In particular, the lancet 86 is pivotally coupled to the test strip 32 via a pivot pin 88. The lancet 86 as well as the pivot pin 88 is positioned within a lancet channel 90 that has a generally circular shape to permit rotation of the lancet 86, while minimizing the size of the lancet channel 90. Again, it should be recognized that the lancet channel 90 can be shaped differently in other embodiments. The lancet 86 includes a lancet body 50 from which a lancet tip 52 extends for forming an incision in skin. The lancet body 50 is wider than the lancet tip 52 so as to form penetration edge 53, which acts to control the penetration depth of the lancet 86 and vertically position the capillary opening 40 relative to the skin. The lancet body 50 defines one or more pivot openings 92, which are located radially outward from the pivot pin 88 in order to permit the application of torque to rotate the lancet 86. The lancet 86 in the illustrated embodiment has two pivot openings 92 located on opposite sides of the pivot pin 88. Nevertheless, it should be understood that the lancet 86 can have more or less pivot openings 92 than is shown, and the pivot openings 92 can be shaped differently. As should be further recognized, the lancet 86 can be modified to be rotated by other types of mechanisms.

Figure 14:
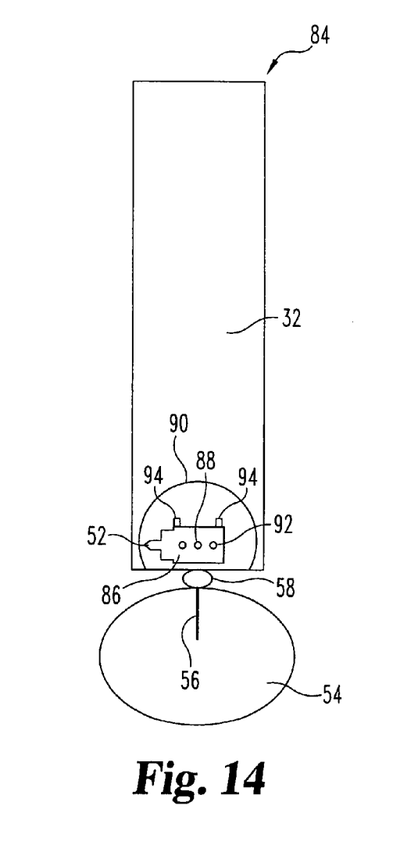
FIG. 14 shows the FIG. 10 device with the lancet in a fully retracted position for collecting fluid from the incision.

The integrated device 84 in FIG. 11 has a retention mechanism or structure 93 acts like a detent mechanism to fix the orientation of the lancet 86 relative to the test strip 32. In the FIG. 11 embodiment, the retention mechanism 93 includes one or more retention pins or dimples 94. The lancet 86 is held rotationally fixed or immovable relative to the test strip 32 by two retention pins 94 positioned on opposing sides of the lancet 86, when the lancet 86 is in an extended position. In one form, the pins 94 are in the form of plastic protrusions extending within the lancet channel 90, but it should be understood that the pins 94 can be formed from other materials. The pins 94 can be also oriented in other manners than is shown. Further, it is envisioned that other types of retention mechanisms or structures 93 can be used. In the illustrated embodiment, the lancet tip 52 is covered by protective cover 42 to maintain the sterility of the lancet 86 and prevent accidental punctures. As mentioned before, by having the lancet 86 in an immovable state, the protective cap 42 can be easily removed prior to use. In another embodiment, the lancet 86 prior to use is oriented such that the lancet tip 52 is positioned within the lancet channel 90, as is shown in FIG. 14. With the lancet tip 52 inside the lancet channel 90, the risk of accidental injury is reduced. To maintain the sterility of the lancet 86, the opening of the lancet channel 90 can be sealed and/or the entire integrated device 84 can be packaged in a sterile enclosure.

Figure 12:
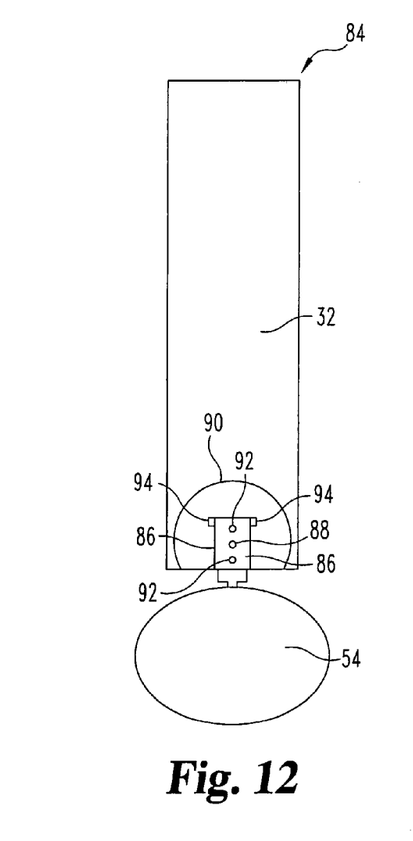
FIG. 12 shows the FIG. 10 device lancing the skin to form an incision.
Figure 13:
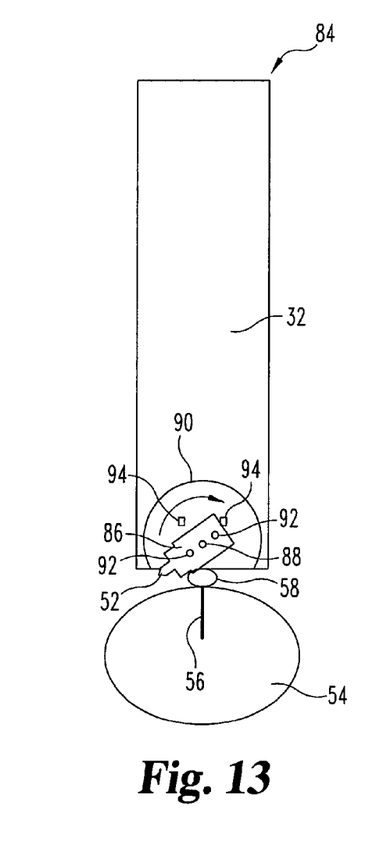
FIG. 13 shows the FIG. 10 device as the lancet is retracted from the incision.

FIGS. 12, 13 and 14 illustrate the various stages of sampling fluid from an incision with the integrated lancing test strip 84. Looking at FIG. 12, the entire integrated device 84 is fired against the skin 54 with the lancet 86 in an immovable position in which the lancet tip 52 extends from the test strip 32. The retention pins 94 retain the lancet 86 in the fixed position relative to the test strip 32. After forming the incision 56 in the skin 54, the lancet 86 is retracted via a rotational motion, as is depicted in FIGS. 13 and 14. Before rotating the lancet 86, the integrated device 84 in one embodiment is pulled away slightly from the skin 54 so that the lancet tip 52 is removed from the incision 56. In another embodiment, the lancet 86 is rotated while still in the incision 56 such that the incision 56 is enlarged. By enlarging the incision 56, a greater amount of body fluid 58 can bleed from the incision 56 at a given penetration depth. Automatic or manual expression of fluid 58 from the incision 56 can occur, if needed, after the incision 56 is formed.

To rotate the lancet 86, the opposing pin openings 92 in one embodiment are engaged by a modified version of the stabilizer/retractor arm 66 (FIG. 6), which includes two engagement pins 68 for engaging the pin openings 92. The modified retractor arm 66 in this embodiment includes an electric motor to rotate the engagement pins 68. However, in other embodiments, other mechanisms that perform a similar function, such as pneumatic motors, linkages, pulleys and the like, can be used. Moreover, it is contemplated that the lancet 86 can be rotated in other manners. As pressure is applied when rotation is initiated, the retention pins 94 give way to allow rotation of the lancet 86. As can be seen in FIG. 14, the lancet 86 continues to rotate until one side of the lancet 86 engage both retention pins 94 so that the lancet tip 52 is positioned inside the integrated device 84. If so desired, the lancet 86 can be further rotated and locked in position such that the lancet tip 52 extends away from the incision 56. With the retention pins 94 engaging to one side of the lancet 86, the lancet 86 is unable to protrude from the test strip 32, unless an outside force is applied. As such, the droplets of body fluid 58 can be drawn into the capillary channel 40 of the test strip 32 without the lancet 86 interfering with fluid collection. In one form, the modified version of the actuation device 60 in FIG. 6 can be used to bend the test strip 32 to swipe the test strip across the incision 54. In another embodiment, the test strip 84 can collect fluid without the flexing or swiping motion. It also is envisioned that portions of the integrated device 84 can be made, treated and/or configured to be hydrophobic or hydrophilic so as to direct the flow of the body fluid 58. For instance, the lancet channel 90 in one form is coated with a hydrophobic coating so that the body fluid 58 is directed away from the lancet channel 90.

Figure 15:
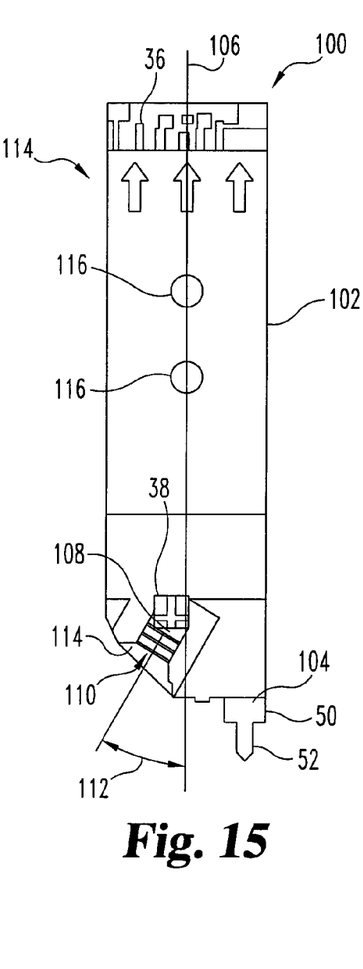
FIG. 15 is a top view of an integrated lancing test strip device according to a further embodiment.

An integrated lancing test strip device 100, according to another embodiment, that uses a rotational motion to collect fluid will now be described with reference to FIGS. 15, 16, 17 and 18. As can be seen in FIG. 15, the integrated device 100 shares a number features in common with the previously described embodiments. Once more, for the sake of clarity as well as brevity, these common features will not be again described in great detail below, but reference is made to the previous description of these features.

As mentioned before, some previous integrated disposable designs were proposed in which a lancet is fixed to a body that holds a separate sensor, which is then rotated into position to collect body fluid. However, the body for such type of disposable was typically made from an extruded plastic that made them rather bulky and expensive to manufacture. Due to their bulky nature, these types of disposables were difficult to incorporate into magazines, drums, cassettes or cartridges. In contrast, the shape of the integrated lancing test strip 100 in the FIG. 15 embodiment is generally flat and compact, which makes the integrated lancing test strip 100 ideal for magazines, drums, cassettes, cartridges and the like. Manufacturing of the FIG. 15 integrated lancing test strip 100 is also simpler as compared to the prior disposable designs. For example, the integrated lancing test strip 100 in one embodiment is formed by layering and adhering a series of material strips or sheets, which is ideal for a continuous manufacturing process. The integrated lancing test strip 100 also eliminates the need for a separate body.

As shown, the integrated device 100 includes a test strip 102 with connector portion 36 and a lancet 104 that is coupled the test strip 102. In the illustrated embodiment, the lancet 104 is fixed to the test strip 102. However, the lancet 104 in other embodiments is coupled to the test strip 102 in a moveable manner, such as in the embodiments previously described. For example, the lancet 104 can be coupled to the test strip 102 through a detent mechanism that allows the lancet 104 to retract inside the integrated device 100 such that the lancet 104 does not interfere with fluid collection. In the FIG. 15 embodiment, the test strip 102 is an electrochemical type test strip, but it should be appreciated that other types of test strips can be used, such as a colorimetric type test strip. As can be seen, the lancet 104 is positioned offset from the central longitudinal axis 106 of the integrated device 100 such that the lancet 104 extends along one side of the test strip 102, parallel to the longitudinal axis 106. To provide a compact profile, the lancet 104 in the depicted embodiment is generally flat, and the lancet 104 includes a lancet tip 52 for forming an incision in tissue and a body portion 50 that connects the lancet tip 52 to the rest of the lancet 104.

Referring to FIG. 15, the test strip 102 defines a capillary channel 108 that has an analysis portion 38 for analyzing the fluid sample. The capillary channel 108 has an opening 110 that is offset from the longitudinal axis 106 of the test strip 102 and slanted at an angle 112 relative to the longitudinal axis 106. In one form, the angle 112 between the capillary opening 110 and the longitudinal axis 106 is an oblique angle. As shown, the capillary channel 108 has a boomerang shape, and the capillary channel opening 110 is Y-shaped with a curved opening. However, it is envisioned that the channel 108 can be shaped differently in other embodiments. The illustrated test strip 102 has a generally rectangular shape, with the exception that the test strip 102 has a truncated corner 114 at the capillary channel opening 110. The truncated corner 114 allows the capillary channel opening 110 to be rotated over the incision site without having the test strip 102 contacting the skin or the body fluid drop, which could potentially smear the drop of fluid.

By having the ability to rotate the lancet 104 out of the way, the capillary channel 108 is able to collect the fluid sample without the lancet 104 interfering with the sample collection. In some embodiments, the integrated device 100 is rotated between 30° to 180° to collect the fluid sample. To minimize the rotation of the test strip 102, the lancet 104 and the capillary channel 108 are located near the same end of the test strip 102. It is nonetheless contemplated that the lancet 104 and the capillary channel 108 can be positioned differently for other embodiments. For example, the orientation of the lancet 104 and the capillary channel 108 can be reversed such that the capillary channel 108 extends parallel to the longitudinal axis 106 and the lancet 104 extends in a nonparallel manner relative to the longitudinal axis 106. The integrated lancing test strip 100 in one form is rotated manually by the user after the incision is formed, and in another form, the meter automatically rotates the integrated lancing test strip 100. To automatically rotate the integrated device 100, the integrated device 100 includes a coupling structure 114 that allows a modified version of the FIG. 6 actuating device 60, or some other type of meter, to rotate the integrated device. In the illustrated embodiment, the test strip 102 has one or more engagement holes 116 through which the test strip 102 is held and rotated. It is envisioned that other types of coupling structures with different configurations can be used to rotate the integrated device 100.

Figure 16:
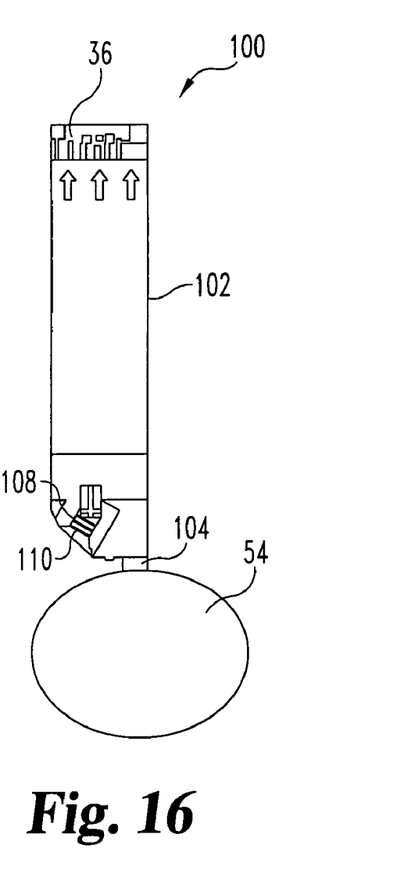
FIG. 16 shows the FIG. 15 device lancing the skin to form an incision.
Figure 17:
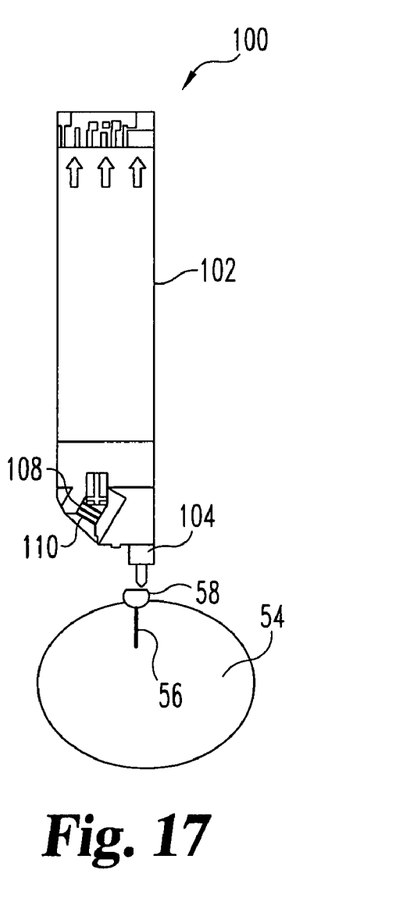
FIG. 17 shows the FIG. 15 device as the lancet is retracted from the incision.
Figure 18:
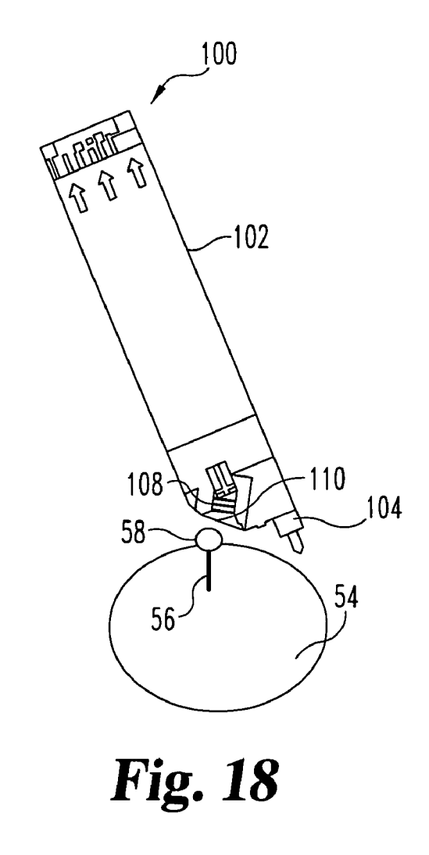
FIG. 18 shows the FIG. 15 device positioned to sample body fluid from the incision.

Referring now to FIGS. 16, 17 and 18, there is illustrated the various stages for collecting and analyzing a body fluid sample with the integrated device 100. As shown in FIG. 16, the lancet 104 lances the skin 54 by having the entire integrated lancing device 100 fired towards the skin 54. After rupturing the skin 54, the entire integrated device 100 is then retracted from the skin 54 so as to promote fluid flow from the incision 56, as is illustrated in FIG. 17. If needed, after the incision 56 is formed, body fluid 58 can be manually or automatically expressed by stimulating the skin 54 surrounding the incision 56. Once a sufficient amount of fluid 58 collects on the skin 54, the entire integrated device 100 is rotated so that the capillary channel 108 is able to collect body fluid 58 from the incision 56, as is depicted in FIG. 18. The test strip 102 is rotated such the lancet 104 moves away giving a clear path for the capillary 108 of the test strip 102 to contact the body fluid 58. In the embodiment where the lancet 104 is not fixed to the test strip 102, the lancet 104 can be retracted inside the integrated device 100 so as to further reduce the chance of the lancet 104 interfering with fluid collection and the risk of accidentally stabbing with the lancet 104. As mentioned before, the integrated device 100 can be rotated manually by the user, for example by repositioning the entire meter, or the entire integrated lancing device 100 can be rotated automatically by the meter. The body fluid 58 is then drawn by the capillary channel 108 into the analysis area 38 where the sample is analyzed. In the illustrated embodiment, the integrated device 100 is connected to a signal converter or meter through the strip connector 36, and the results from the analysis are transferred to the meter through the connector 36.

While the invention has been illustrated and described in detail in the drawings and foregoing description, the same is to be considered as illustrative and not restrictive in character. It should be understood that only the preferred embodiment has been shown and described and that all changes and modifications that come within the spirit of the invention are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A method, comprising:
holding a lancet in a fixed position relative to a test strip of an integrated lancing test strip device where at least a portion of the lancet extends from a distal end of the test strip that faces a tissue;
forming an incision in the tissue with the portion of the lancet extending from the distal end of the test strip;
releasing the lancet from the fixed position;
retracting the lancet after said forming the incision, wherein said retracting includes rotating the lancet relative to the test strip where the portion of the lancet is located inside the distal end of the test strip; and
collecting body fluid from the incision with the test strip after said retracting the lancet.

2. The method of claim 1, wherein said releasing the lancet occurs after said forming the incision.

3. The method of claim 1, further comprising:
wherein said collecting includes swiping the test strip over the body fluid from the incision with a deflection mechanism.

4. The method of claim 1, further comprising:
removing a protective cover from the lancet before said forming the incision.

5. The method of claim 4, further comprising:
wherein the protective cover includes a plastic cap; and
wherein said removing the protective cover includes pulling the plastic cap off the lancet.

6. An apparatus, comprising:
an integrated lancing test strip device including
a test strip for analyzing body fluid, the test strip having a capillary channel with an opening at a distal end of the test strip for drawing the body fluid via capillary action,
a lancet directly coupled to the test strip for forming an incision in tissue, wherein the lancet is pivotally coupled to the test strip, and
a pivot pin pivotally coupling the lancet to the test strip to allow the lancet rotate relative to the test strip; and
an actuation device coupled to the integrated lancing test strip device, the actuation device being configured to fire the lancet into the tissue, wherein the actuation device is configured to rotate the lancet away from the incision in order to minimize interference by the lancet as the body fluid from the incision is drawn into the capillary channel of the test strip, wherein the actuation device is configured to rotate the lancet relative to the test strip from a position where the lancet extends past the distal end of the test strip to a position where the lancet is retracted inside the distal end of the test strip.

7. The apparatus of claim 6, further comprising:
a retention mechanism holding the lancet fixed relative to the test strip.

8. The apparatus of claim 7, further comprising:
the retention mechanism including one or more retention pins.

9. The apparatus of claim 7, further comprising:
the lancet including a lancet tip configured to form the incision in the tissue; and
the retention mechanism holding the lancet at an orientation where the lancet tip extends from the test strip.

10. The apparatus of claim 9, further comprising:
a protective cover covering the lancet tip.

11. The apparatus of claim 10, wherein the protective cover includes a plastic cap configured to be pulled off the lancet tip.

12. The apparatus of claim 7, wherein the retention mechanism is configured to hold the lancet in position after the lancet is rotated.

13. The apparatus of claim 6, wherein the test strip includes an analysis portion that includes a reagent and electrodes for analyzing the body fluid.

14. An apparatus, comprising:
an integrated lancing test strip device including
a test strip including a capillary channel with an opening for drawing body fluid via capillary action and a reagent for analyzing the body fluid, the test strip having a distal end at the opening of the capillary channel,
a pivot pin coupled to the test strip,
a lancet pivotally coupled by the pivot pin to the test strip, the lancet being able to rotate relative to the test strip via the pivot pin, and
a retention mechanism holding the lancet in an extended state relative to the distal end of the test strip during lancing, the retention mechanism being configured to release the lancet during retraction to allow the lancet to rotate relative to the test strip, the retraction mechanism being configured to hold the lancet in a retracted state inside the distal end of the test strip.

15. The apparatus of claim 14, in which the retention mechanism includes a pair of retention dimples located on opposing sides of the lancet to hold the lancet in the extended state relative to the test strip during lancing.

16. The apparatus of claim 15, further comprising:
an actuation device coupled to the integrated lancing test strip device, the actuation device being configured to fire the lancet into tissue in a linear direction with the lancet in the extended state, the actuation device being configured to rotate the lancet relative to the test strip.

17. The apparatus of claim 16, further comprising:
the lancet having a pair of pin openings located on opposing sides of the pivot pin; and
the actuation device having a pair of engagement pins engageable with the pin openings to rotate the lancet relative to the test strip.

18. A method, comprising:
holding a lancet in an extended state relative to a test strip of an integrated lancing test strip device with a retention mechanism, wherein at the extended state at least a portion of the lancet extends from a distal end the test strip, wherein the lancet is pivotally coupled to the test strip via a pivot pin and the retention mechanism holds the lancet in the extended state;
forming an incision in tissue with the lancet in the extended state by moving the integrated lancing test strip device in a linear direction into the tissue;
retracting the lancet to a retracted state after said forming the incision by rotating the lancet relative to the test strip about the pivot pin, wherein the retention mechanism releases the lancet to allow the lancet to rotate during said retracting;
securing the lancet in the retracted state with the retention mechanism where the lancet is rotated inside the distal end of the integrated lancing test strip device as a result of said retracting; and
collecting body fluid from the incision with the test strip after said retracting the lancet.

19. The method of claim 18, further comprising:
wherein said collecting includes swiping the test strip over the body fluid from the incision with a deflection mechanism.

20. The method of claim 18, further comprising:
removing a protective cover from the lancet before said forming the incision.

21. The method of claim 20, further comprising:
wherein the protective cover includes a plastic cap; and
wherein said removing the protective cover includes pulling the plastic cap off the lancet.

* * * * *